United States Patent
Medon et al.

(10) Patent No.: US 9,044,691 B2
(45) Date of Patent: Jun. 2, 2015

(54) METHOD AND APPARATUS FOR DEHYDRATION OF GLYCOL

(76) Inventors: Piotr Medon, Wroclaw (PL); Edward Reszke, Wroclaw (PL)

(*) Notice: Subject to any disclaimer, the term of this patent is extended or adjusted under 35 U.S.C. 154(b) by 643 days.

(21) Appl. No.: 13/312,362

(22) Filed: Dec. 6, 2011

(65) Prior Publication Data

US 2012/0318659 A1  Dec. 20, 2012

(30) Foreign Application Priority Data

Jun. 20, 2011 (PL) .......................................... 395358

(51) Int. Cl.
*B01D 1/00* (2006.01)
*B01D 3/00* (2006.01)
*C07C 29/76* (2006.01)
*C07C 29/80* (2006.01)

(52) U.S. Cl.
CPC .............. *B01D 1/0017* (2013.01); *C07C 29/76* (2013.01)

(58) Field of Classification Search
CPC ...... C07C 29/74; C07C 29/76; C07C 31/202; B01D 1/0017; H01M 2/26; H01L 23/48; H01L 23/66; Y10S 159/26; Y10S 203/90; Y10S 204/07; Y10S 204/08
See application file for complete search history.

(56) References Cited

U.S. PATENT DOCUMENTS

| | | | | |
|---|---|---|---|---|
| 1,885,393 A | * | 11/1932 | Van Schaack, Jr. | 210/644 |
| 2,121,954 A | * | 6/1938 | Cunningham | 205/450 |
| 3,180,814 A | * | 4/1965 | Kollsman | 205/688 |
| 3,323,954 A | * | 6/1967 | Goorissen | 117/99 |
| 3,508,167 A | * | 4/1970 | Russell, Jr. | 331/111 |
| 4,427,507 A | * | 1/1984 | van Aken et al. | 204/522 |
| 4,671,874 A | * | 6/1987 | Fremont et al. | 204/627 |
| 4,942,361 A | * | 7/1990 | Gast et al. | 324/360 |
| 5,766,447 A | * | 6/1998 | Creijghton | 205/742 |
| 5,895,558 A | * | 4/1999 | Spence | 204/164 |
| 6,005,218 A | * | 12/1999 | Walde et al. | 219/121.54 |
| 6,051,111 A | * | 4/2000 | Prestidge | 203/11 |
| 2008/0308427 A1 | * | 12/2008 | Field | 205/450 |
| 2010/0224493 A1 | * | 9/2010 | Davalos et al. | 204/547 |

FOREIGN PATENT DOCUMENTS

| | | | |
|---|---|---|---|
| GB | 1017134 | * | 1/1966 |
| PL | 195588 B1 | | 9/1999 |
| PL | 196671 B1 | | 9/1999 |

OTHER PUBLICATIONS

Zahn et al "Dielectric Properties of Water and Water/Ethylene Glycol Mixture for Use Pulsed Power System Design"; Proceedings of the IEE, vol. 74, No. 9, Sep. 1986.*

* cited by examiner

*Primary Examiner* — Virginia Manoharan
(74) *Attorney, Agent, or Firm* — Leading-Edge Law Group, PLLC

(57) ABSTRACT

A method and apparatus for dehydration of glycol uses two galvanic electrodes submerged in a water-glycol mixture. Semiconductor switches are used to supply pulses from a direct current source and to control the polarization and current flow time in such a way as to produce an average current of zero and a switching frequency commensurate with electro-hydrodynamic frequency of the electrode and liquid system. By applying sufficiently low frequency of switching, stirring of glycol and removal of gas products from the electrodes is achieved. The glycol container has at least one submerged electrode module equipped with at least two galvanic electrodes. Each electrode is connected through pairs of high power electronic switches which cycle alternatively between the positive and negative terminals of a direct current power supply.

8 Claims, 3 Drawing Sheets

METHOD AND APPARATUS FOR DEHYDRATION OF GLYCOL

BACKGROUND OF THE INVENTION

The invention relates to a method for drying glycol and to a system for removing water from glycol.

Glycols are used in various industries such as refrigeration, heating, petro-chemistry and chemical synthesis. However, the most common application and use for glycol is in the mining industry. Because of a substantial consumption of glycol in technological processes, the removal of water from solutions and recovery of glycol have an important role.

BRIEF DESCRIPTION OF THE PRIOR ART

Dehydration of glycol usually includes thermal water evaporation using variations in partial vapor pressures, i.e. approximately 1.5 mm Hg (200 Pa)/100° C. for glycol and over 1 bar/100° C. for water. This process is complicated by the fact that glycol has a lower thermal decomposition temperature than the boiling temperature which makes the regeneration process difficult. The process is carried out in an apparatus composed of a boiler and a rectification column filled up with Raschig or Bialecki rings. The fundamental element in the process is always the heating of a glycol and water mixture, usually by gas combustion using a heat exchanger or an ohmic heater immersed in the solution, warmed by nitrogen striping gas and also heated by another auxiliary heating medium such as transformer oil or steam.

Methods of heating a glycol and water mixture using an electrical field are also known. In this case it is possible to use gas as a fuel for an electric aggregate and further use electricity. However, three elements which are important from the industrial application point of view are not present in the known solutions to the problem of heating the gas-water mixture. First, when Joule heating is applied the electric current flow is blocked by the gas accumulated on electrodes. Second, the electrical resistance of glycol during heating changes by approximately two orders of magnitude which makes controlling the process difficult and therefore potentially unstable. Third, direct usage of 50/60 Hz alternating current is troublesome because the distribution system of electrical energy has to be split into many containers.

A method of distillation-type recovery of high purity mono-ethylene-glycol (MEG) is known from Polish patent application P195588 and assumes that the stream of water, which contains less than 1% by weight of glycol, and preferably 0.1%, by weight of glycol, along with middle and low boiling substances, are reclaimed after additional processing and removed from the installation. While vacuum dehydration is conducted in the vacuum dehydration column, the stream of water is collected as a side stream from the vacuum dehydration column. Alternatively, the dehydration is carried out in two vacuum dehydration columns and the stream of water is collected as an upper stream of the second vacuum dehydration column. The removal of the secondary elements from the installation is particularly effective when the outflow from the stripping unit is returned to the first dehydration column, because this returning process increases the aldehyde content on top of the first dehydration column and in the stripping unit, and also improves the speed of removal.

During the process, heat is applied below the point of supply of the stream feeding the dehydration column. Its temperature is above 80° C., preferably from 115° C. to 230° C. The pressure in the stripping section does not drop below 0.1 MPa (1 bar) and amounts to 0.2 up to 3 Mpa (2-30 bar).

The upper stream of the pressure dehydration column having the stripping section is fed to a dephlegmator and/or stripping section, preferably into the steam powered stripping section and the stream (streams) enriched with the secondary components which were removed from installation. The dephlegmator and/or stripping sections operate at temperatures in excess of 90° C., in the range of 120° C. up to 250° C.

A method of distillation-type recovery leading to high purity MEG known from Polish patent application P 196671 requires a pressure dehydration column or at least a first column of pressure dehydration and a stripping section with at least one separation step, advantageously with three to six separation steps and most advantageously with two to ten separation steps, where a portion of the upper stream in the column is taken up by means of a removal section. The temperature below the inflow point to the stripping pressure dehydration column in the cascade is over 80° C. while the pressure in the removal section is at least $1 \times 10^5$ Pa. The temperature below the inflow point to the pressure dehydration column in cascade is between 115° C. and 230° C. and the pressure in stripping section is between $2\text{-}30 \times 10^5$ Pa.

The upper stream of the dehydration column or columns with the stripping section is fed to the partial condenser and/or stripping column, particularly the steam-type stripping column, while the stream or streams of gas enriched with by-products are discharged. The partial condenser and the stripping column operate at temperatures above 90° C., preferably between 120° C. and 250° C.

SUMMARY OF THE INVENTION

In a method according to the present invention, galvanic electrodes are immersed in glycol and are supplied with pulses from a direct current source.

Polarization and electric current flow periods are controlled by semiconductor power switches in such a way that the mean algebraic value of current equals zero, and the switch frequency is commensurate with electrohydrodynamic self-frequency of the electrodes immersed in a glycol tank. The alternating current of ions generated by pulsed electric supply of the electrodes with sufficiently low switching frequency causes stirring of glycol and at the same time the electrodes are cleaned of gaseous products.

The apparatus according to the invention includes at least one electrode module immersed in the container equipped with at least two galvanic electrodes, of which at least two are periodically connected by way of semiconductor power switches, in alternating cycles, to the positive and negative current source terminals. Preferably, each electrode is commutated to the positive and negative current source terminals with the use of two semiconductor energo-electronic switches.

The use of direct-current power engineering combined with power-electronic semiconductor switching devices is an important feature of the invention. Its aim is to obtain slow-running alternating current square time-shapes with a regulated filling rate which allows the precise adjustment of average current values and at the same time, due to the selection of the switching frequency being commensurate with the hydrodynamic self frequencies, allows for stirring of glycols during dehydration.

It is worth noting that in order to improve energy efficiency in the dehydration process, part of the heat of the purified mixture is used for initial heating of the mixture supplied to the beginning of the thermal process for recuperation.

BRIEF DESCRIPTION OF THE FIGURES

Other objects and advantages of the present invention will become apparent from a study of the following specification when viewed in the light of the accompanying drawing, inc which.

DETAILED DESCRIPTION

The glycol dehydration system according to a first embodiment of the invention will be described with reference to FIG. 1. The system includes two flat galvanic electrodes $E_1$ and $E_2$ which are immersed in glycol GL stored in a rectangular container ZB. The glycol GL is heated by an electric field generated by Joule currents. Galvanic electrodes $E_1$ and $E_2$ are supplied with pulses from the direct current source $U_{DC}$ by semiconductor power switches $T_{11}$, $T_{12}$, $T_{21}$ and $T_{22}$. They control polarization and current flow times in such a way that the overall mean algebraic current value equals zero, and the switch frequency $1/T$ is commensurate with the electro-hydrodynamic eigenfrequency of the electrodes $E_1$ and $E_2$, the container ZB, and the glycol GL. When alternating current of ions is applied, generated by the pulse-supply of electrodes $E_1$ and $E_2$ with a sufficiently low switch frequency $1/T$, glycol is stirred and at the same time the electrodes $E_1$ and $E_2$ are cleansed of gaseous products. The glycol GL dehydration process takes place under heated conditions with a temperature from 110° C. to 170° C.

Figure 1:
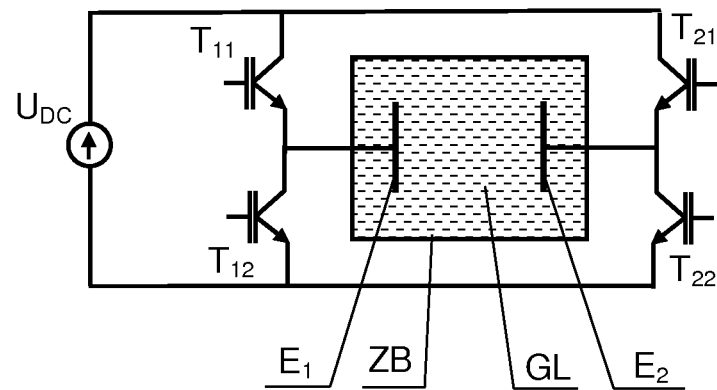
FIG. 1 is a schematic diagram of an electrode module of the system for the dehydration of glycol equipped with two galvanic electrodes.
Figure 2:
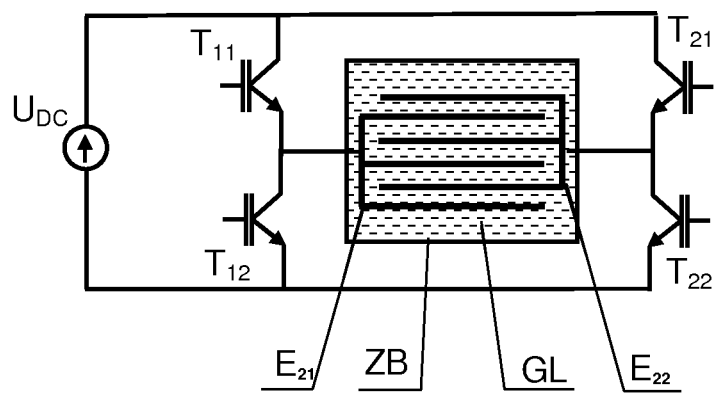
FIG. 2 is a schematic diagram of an electrode module of the system for the dehydration of glycol equipped with two comb-shaped electrodes.

FIG. 2 shows a glycol dehydration system according to a second embodiment of the invention wherein one module of electrodes containing two flat galvanic electrodes $E_{21}$ and $E_{22}$ is immersed in a rectangular container ZB with glycol GL in the same manner as in the embodiment of FIG. 1. Galvanic electrodes $E_{21}$ and $E_{22}$ are comb shaped, with interleaved portions. The electrodes are pulse-commutated in alternating cycles to the positive and negative terminals of direct current source $U_{DC}$ via four power-electronic semiconductor switches $T_{11}$, $T_{12}$, $T_{21}$ and $T_{22}$. The electrode $E_{21}$ is connected to the terminals of the direct current source $U_{DC}$ by two power-electronic semiconductor switches $T_{11}$, $T_{12}$ and the electrode $E_{22}$ is connected with the terminals $T_{21}$, $T_{22}$.

In an alternate embodiment, not shown, a glycol dehydration system is provided similar to that shown in FIG. 2, except that three electrode modules are immersed in the container of glycol. Each module is provided with two comb-shaped galvanic electrodes arranged in an interleaved manner as in the embodiment shown in FIG. 2. The electrodes are connected with a direct current source via semiconductor switches.

Figure 3:
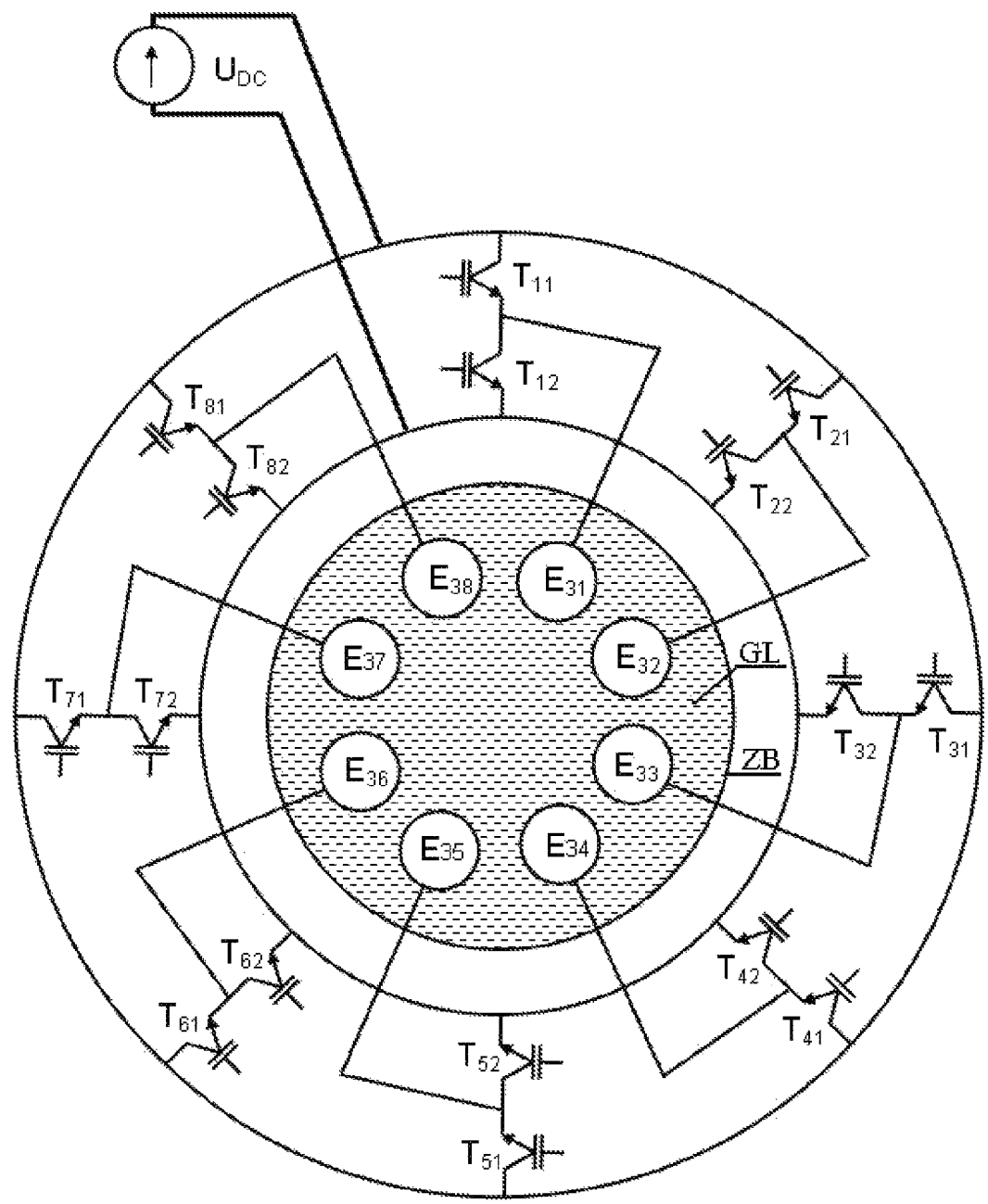
FIG. 3 is a schematic diagram of an electrode module of the system for the dehydration of glycol provided with eight electrodes.

Referring now to FIG. 3, there is shown a glycol dehydration system according to a third embodiment of the invention wherein each electrode module is provided with eight galvanic rod shaped electrodes $E_{31}$, $E_{32}$, $E_{33}$, $E_{34}$, $E_{35}$, $E_{36}$, $E_{37}$ and $E_{38}$ submerged in a cylindrical container ZB filled with glycol GL. Three modules of eight rod shaped electrodes may be provided in the glycol. Each of the galvanic electrodes $E_{31}$, $E_{32}$, $E_{33}$, $E_{34}$, $E_{35}$, $E_{36}$, $E_{37}$ and $E_{38}$ is supplied with pulses from the direct current supply $U_{DC}$ via a pair of power-electronic semiconductor switches. Thus, electrode $E_{31}$ is connected with switches $T_{11}$ and $T_{12}$. Electrode $E_{32}$ is connected with switches $T_{21}$ and $T_{22}$. Electrode $E_{33}$ is connected with switches $T_{31}$ and $T_{32}$. Electrode $E_{34}$ is connected with switches $T_{41}$ and $T_{42}$. Electrode $E_{35}$ is connected with switches $T_{51}$ and $T_{52}$. Electrode $E_{36}$ is connected with switches $T_{61}$ and $T_{62}$. Electrode $E_{37}$ is connected with switches $T_{71}$ and $T_{72}$. Electrode $E_{38}$ is connected with switches $T_{81}$ and $T_{82}$.

The system of FIG. 3 operates in such a way that in the first stage when the heating reaches approximately 100° C., odd galvanic electrodes $E_{31}$, $E_{33}$, $E_{35}$, and $E_{37}$ during the first pulse are connected by semiconductor switches $T_{11}$, $T_{31}$, $T_{51}$ and $T_{71}$ to the positive terminal of the direct current source terminal $U_{DC}$, while even galvanic electrodes $E_{32}$, $E_{34}$, $E_{36}$, and $E_{38}$ are connected to the negative terminal of the direct current source terminal $U_{DC}$ via power semiconductor switches $T_{22}$, $T_{42}$, $T_{62}$ and $T_{82}$. During the second pulse, odd galvanic electrodes $E_{31}$, $E_{33}$, $E_{35}$, and $E_{37}$ are connected by semiconductor switches $T_{22}$, $T_{42}$, $T_{62}$ and $T_{82}$ to the negative terminal of the direct current source terminal $U_{DC}$, while even galvanic electrodes $E_{32}$, $E_{34}$, $E_{36}$, and $E_{38}$ are connected to the positive terminal of the direct current source terminal $U_{DC}$ via power semiconductor switches $T_{21}$, $T_{41}$, $T_{61}$ and $T_{81}$. This process changes cyclically until the glycol GL is heated to a temperature above 100° C.

In the second stage of the operation of the system, further pairs of electrodes $E_{31}$ and $E_{35}$, $E_{32}$ and $E_{36}$, $E_{33}$ and $E_{37}$, $E_{34}$ and $E_{38}$ are cyclically connected to the positive and negative direct current terminals $U_{DC}$. Due to commutation of electrodes $E_{31}$, $E_{32}$, $E_{33}$, $E_{34}$, $E_{35}$, $E_{36}$, $E_{37}$ and $E_{38}$ with power-electronic semiconductor switches $T_{11}$, $T_{12}$, $T_{21}$, $T_{22}$, $T_{31}$, $T_{32}$, $T_{41}$, $T_{42}$, $T_{51}$, $T_{52}$, $T_{61}$, $T_{62}$, $T_{71}$, $T_{72}$, $T_{81}$, and $T_{82}$ with a sufficiently low frequency commensurate with the time constant characterizing the near electrode processes, stirring of glycol GL is additionally achieved which significantly improves the efficiency of the dehydration process. The dehydration of glycol GL is conducted with the rising temperature adequate for the specific types of glycol, i.e. from 100° C. to 250° C.

Figure 4:
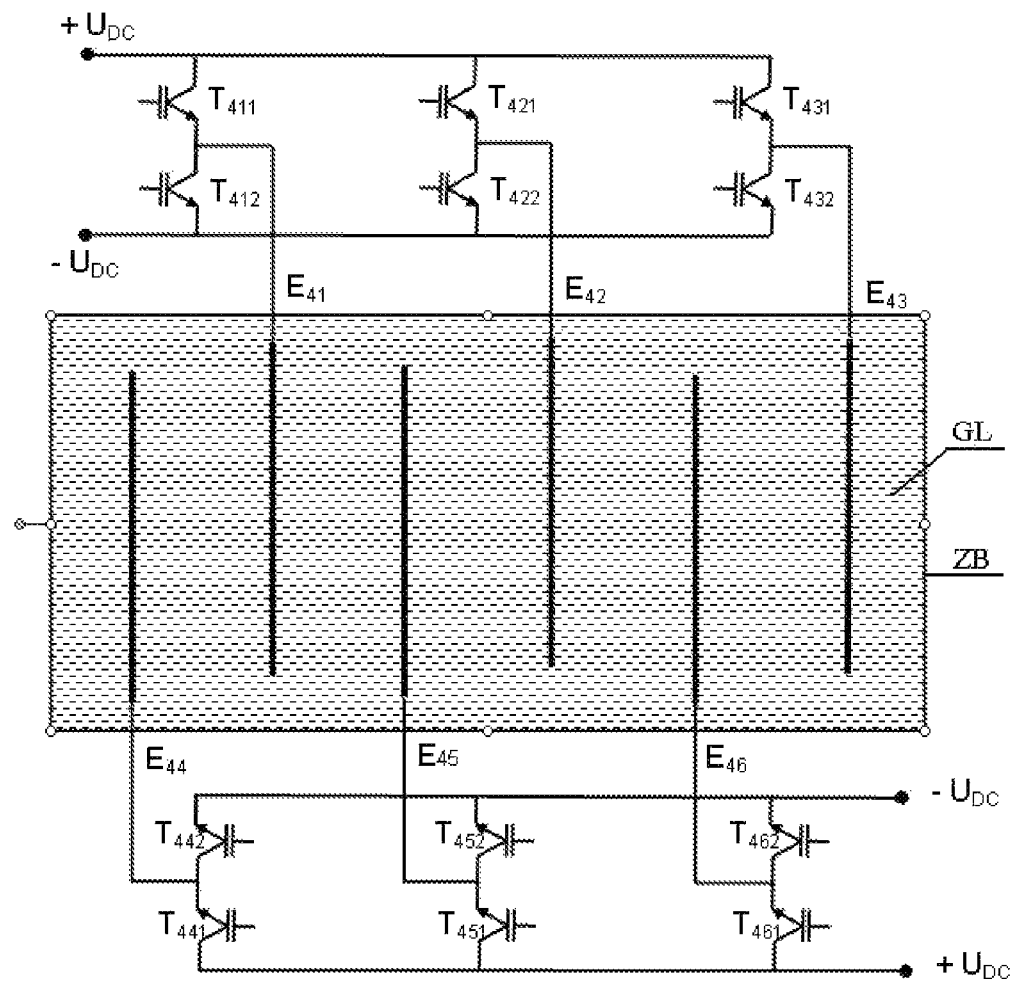
FIG. 4 is a schematic diagram of an electrode module of the system for the dehydration of glycol provided with six galvanic electrodes.

FIG. 4 shows a fourth embodiment of the invention. The glycol dehydration system is operated in the same manner as the system shown in FIG. 1 except that it has two electrode modules, each provided with six flat galvanic rod electrodes $E_{41}$, $E_{42}$, $E_{43}$, $E_{44}$, $E_{45}$ and $E_{46}$ which are connected via twelve power semiconductor switches $T_{411}$, $T_{412}$, $T_{421}$ and $T_{422}$ ... and $T_{462}$ which deliver pulses of current from the direct current source $U_{DC}$. It is worth noting that the geometric configuration and the number of electrodes $E_{41}$ ... $E_{4N}$ can be selected depending on the arrangement of the system, such as the shape of the container ZB for the glycol GL, its linear dimensions and capacity. For example, in a very slender container it is preferable to use a system of electrodes $E_{41}$ ... $E_{4N}$, each in the form of a cylindrical condenser. In a non-slender container with a rectangular shape, it is desirable to use a system of electrodes $E_{41}$ ... $E_{4N}$ each in the form of a flat plate condenser. Control of the effective values of current amperage of electrodes $E_{41}$ ... $E_{4N}$ is accomplished in one of three ways: by grouping the electrodes; by external control of direct current source voltage $U_{DC}$, for instance, using an electronically controlled rectifier; and by using pulse-modulation of the pulse width obtained through the application of power semiconductor switches $T_{411}$ ... $T_{4N2}$ controlled by the low signal digital systems which may be under microprocessor control. Additionally, the electrodes are supplied with a sufficiently low switch frequency 1/T amounting, for example, to approximately 2 Hz.

While the preferred forms and embodiments of the invention have been illustrated and described, it will be apparent to those of ordinary skill in the art that various changes and modifications may be made without deviating from the inventive concepts set forth above.

What is claimed is:

1. A glycol dehydration device, comprising
   (a) a cylindrical container for holding a quantity of glycol;
   (b) a plurality of cylindrical galvanic electrodes arranged within said container in parallel spaced relation in a radial array, said container and each of said plurality of cylindrical galvanic electrode having axes which are parallel;
   (c) a direct current source for supplying direct current; and
   (d) at least one switch connected between said direct current source and said each of said plurality of galvanic electrodes for supplying alternating positive and negative pulses of direct current to each of said plurality of galvanic electrodes at a frequency commensurate with an electro-hydrodynamic eigenfrequency of said plurality of galvanic electrodes, said container, and the glycol to heat the glycol to a temperature sufficient for dehydration.

2. A glycol dehydration device as defined in claim 1, wherein said at least one switch comprises a semiconductor switch.

3. A glycol dehydration device as defined in claim 1, wherein a pair of switches are provided for each of said plurality of cylindrical galvanic electrodes.

4. A glycol dehydration device as defined in claim 1, wherein each of said plurality of galvanic electrodes has a flat configuration with said electrodes being arranged opposite each other in spaced relation.

5. A glycol dehydration device as defined in claim 1, wherein each said plurality of galvanic electrodes has a comb-shaped configuration with said electrodes being arranged in an interleaved manner.

6. A glycol dehydration device as defined in claim 1, wherein said glycol is heated to a temperature from 110° C. to 170° C.

7. A method for removing water from glycol, comprising the steps of
   (a) arranging at least one pair of galvanic electrodes in a container of glycol; and
   (b) sequentially supplying pulses of direct current in alternate polarities to said at least one pair of galvanic electrodes to heat the glycol to a temperature sufficient for dehydration, wherein said pulses are supplied from a direct current source via a plurality of switches which control the pulse polarization and duration and wherein a mean algebraic value of the current equals zero and a switching frequency of polarity of the pulses of direct current is commensurate with an electro-hydrodynamic eigenfrequency of said at least one pair of galvanic electrodes, the container, and the glycol.

8. A method as defined in claim 7, wherein said temperature is from 110° C. to 170° C.

* * * * *